US011375708B2

United States Patent
Gaugler et al.

(10) Patent No.: US 11,375,708 B2
(45) Date of Patent: Jul. 5, 2022

(54) METHODS AND APPARATUS FOR MANAGEMENT OF MOSQUITO POPULATIONS WITH HABITAT SHARING HETEROSPECIFIC INSECTS CARRYING INSECT GROWTH REGULATORS

(71) Applicant: Rutgers, The State University of New Jersey, Piscataway, NJ (US)

(72) Inventors: Randy R. Gaugler, North Brunswick, NJ (US); Devi S. Suman, Kolkata (IN); Bo Tao, South River, NJ (US); Yi Wang, South River, NJ (US)

(73) Assignee: Rutgers, The State University of New Jersey, Piscataway, NJ (US)

( * ) Notice: Subject to any disclaimer, the term of this patent is extended or adjusted under 35 U.S.C. 154(b) by 1002 days.

(21) Appl. No.: 15/997,212

(22) Filed: Jun. 4, 2018

(65) Prior Publication Data

US 2018/0279605 A1    Oct. 4, 2018

Related U.S. Application Data

(63) Continuation-in-part of application No. PCT/US2016/064976, filed on Dec. 5, 2016.
(Continued)

(51) Int. Cl.
*A01M 99/00* (2006.01)
*A01N 25/00* (2006.01)
(Continued)

(52) U.S. Cl.
CPC ........... *A01M 99/00* (2013.01); *A01K 67/033* (2013.01); *A01N 25/00* (2013.01); *A01N 25/02* (2013.01);
(Continued)

(58) Field of Classification Search
CPC ........ A01M 1/10; A01M 1/20; A01M 1/2005; A01M 1/2016; A01M 1/2022; A01M 5/00;
(Continued)

(56) References Cited

U.S. PATENT DOCUMENTS

| 1,990,966 | A | * | 2/1935 | Volck | A01N 25/12 424/409 |
| 2,204,511 | A | | 6/1940 | Ralston et al. | |

(Continued)

FOREIGN PATENT DOCUMENTS

EP        0367934 A1 *  5/1990    ............. A01N 59/00

OTHER PUBLICATIONS

R. Gaugler et al., "An autodisseminatio station for the transfer of an insect growth regulator to mosquito oviposition sites", Med. Vet. Entomol, 26(1): 37-45 (2012).
(Continued)

*Primary Examiner* — Peter M Poon
*Assistant Examiner* — Danielle A Clerkley
(74) *Attorney, Agent, or Firm* — Kathleen D. Rigaut; Howson & Howson LLP

(57) ABSTRACT

Compositions and heterodissemination methods for controlling unwanted target insect populations are disclosed. In preferred embodiments, the target insects are mosquitos or house flies and the heterospecific insects are non-biting midges and soldier flies respectively.

15 Claims, 8 Drawing Sheets

Related U.S. Application Data

Figure 1:
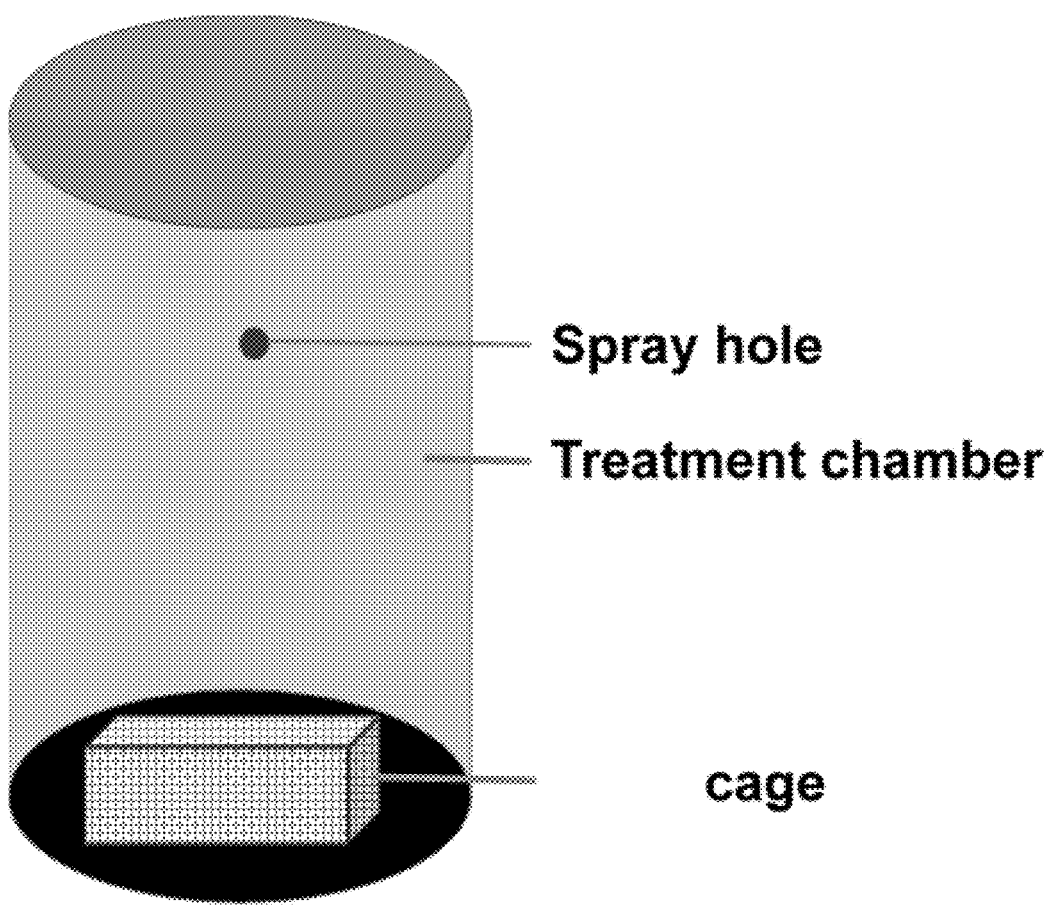

(60) Provisional application No. 62/263,280, filed on Dec. 4, 2015.

(51) Int. Cl.
*A01N 43/40* (2006.01)
*A01N 25/34* (2006.01)
*A01N 63/14* (2020.01)
*A01N 63/23* (2020.01)
*A01K 67/033* (2006.01)
*A01N 25/02* (2006.01)
*A01N 25/12* (2006.01)

(52) U.S. Cl.
CPC .............. *A01N 25/12* (2013.01); *A01N 25/34* (2013.01); *A01N 43/40* (2013.01); *A01N 63/14* (2020.01); *A01N 63/23* (2020.01)

(58) Field of Classification Search
CPC ......... A01M 5/02; A01N 25/02; A01N 25/04; A01N 25/06; A01N 25/12; A01N 25/14
USPC .... 43/124, 125, 129, 131, 132.1; 220/23.83, 220/23.86, 23.87, 23.88
See application file for complete search history.

(56) References Cited

U.S. PATENT DOCUMENTS

| | | | | |
|---|---|---|---|---|
| 7,198,797 | B2* | 4/2007 | O'Brien | A01N 63/23 424/406 |
| 9,192,151 | B2* | 11/2015 | Koehler | A01M 1/04 |
| 9,265,247 | B2* | 2/2016 | Gaugler | A01M 1/2011 |
| 2009/0275601 | A1* | 11/2009 | Taylor | A01N 43/40 514/277 |
| 2010/0123104 | A1 | 5/2010 | Collins et al. | |
| 2013/0259846 | A1 | 10/2013 | Dobson | |
| 2013/0303574 | A1 | 11/2013 | Gaugler et al. | |

OTHER PUBLICATIONS

Habashy, M.M. et al., "Culture of Chrionomid larvae (Insecta-Diptera Chironomidae) under different feeding systems", Egyptian J. Aquat. Res., 31(2):L 403-418 (2005).

Hribar, L.J. et al.,, Mosquito Larvae (Culicidae) and Other Diptera Associated with Containers, Storm Drains, and Sewage Treatment Plants in the Florida Keys, Monroe County, Florida, Florida Entomologist, 87(2): 199-203 (2004).

Shepard, Donald S. et al., "Economic Evaluation of an Area-Wide Integrated Pest Management Program to Control the Asian Tiger Mosquito in New Jersey", Ed. Kristin Michel, PLoS ONE, 9.10 (2014): e111014, PMC. Web. Dec. 1, 2015.

Utgerg, G. et al., The Temporal Distribution of Chironomus decorus (Chironomidae) in Northern New Jersey, Journal of the New York Entomological Society, 16-25 (1979).

Wang, Y, et al., "Dual-treatment Autodissemination station with enhanced transfer of an Insect Growth Regulator to Mosquito Oviposition Sites", Pest Management Science (2014).

International Search Report/Written Opinion issued in corresponding International Application No. PCT/US2016/064976, filed Dec. 5, 2016.

* cited by examiner

Fig. 6A
Fig. 6B
Fig. 7
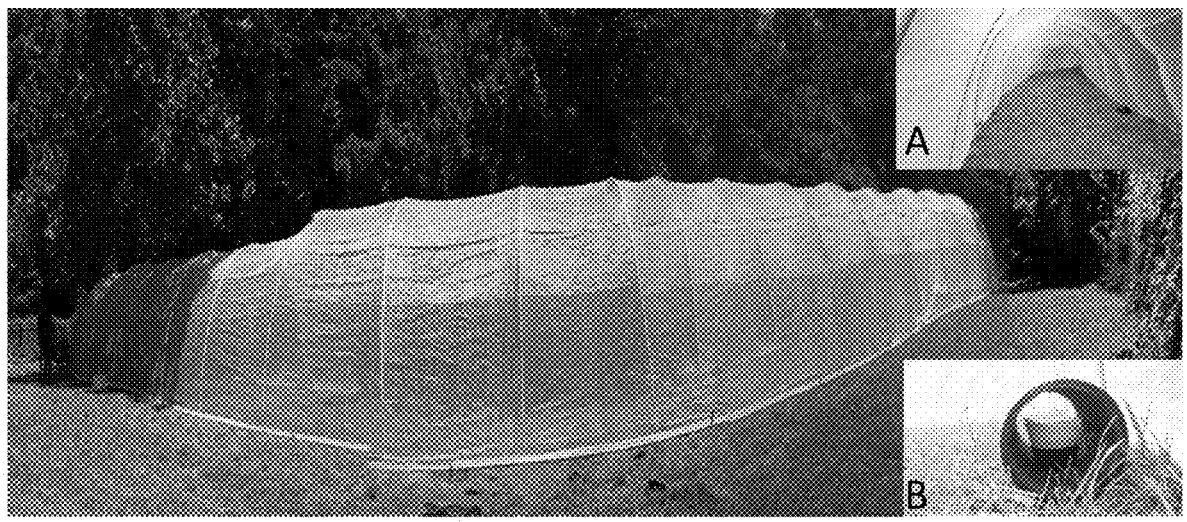

Heterodissemination Technology for container Mosquito Control

Licensed Technology:
- Midges, reproduction & care package
- Formulations (possibly as trade-secret)
- Release techniques (drones, manual)
- Methods of application patents

Midge cage: Grown by Licensee. Sold with Midge reproduction/care instructions

Spray: Oil + powder formulation containing a.i. adheres to midges

Release: Cage placed in downwind vicinity of larvae. Midges carry actives to larval cryptic nest, in appropriate formulation

Destination: Mosquito larval habitat

Figure 10

METHODS AND APPARATUS FOR MANAGEMENT OF MOSQUITO POPULATIONS WITH HABITAT SHARING HETEROSPECIFIC INSECTS CARRYING INSECT GROWTH REGULATORS

This application is a continuation-in-part of PCT/US2016/064976 filed Dec. 5, 2016 which claims priority to U.S. Provisional Application No. 62/263,280 filed Dec. 4, 2015, the entire disclosure of each being incorporated herein by reference as though set forth in full.

FIELD OF THE INVENTION

This invention relates to the fields of mosquito control and more specifically, involves a targeted technology for effective delivery of sufficient amount of pesticide levels into mosquito breeding sites to inhibit adult emergence. The inventive approach minimizes harmful impacts to the environment and does not exhibit adverse effects on mammalians or other beneficial species.

BACKGROUND OF THE INVENTION

Several publications and patent documents are cited throughout the specification in order to describe the state of the art to which this invention pertains. Each of these citations is incorporated herein by reference as though set forth in full.

Globalization and the expansion of transcontinental shipment of tires and other goods in the 1970s led to the worldwide spread of an Asian mosquito species, *Aedes albopictus* (Skuse), and its establishment in new regions and countries around the globe. In the United States, the first established population of *Ae. albopictus* was detected in Harris County, Tex. in 1985. Since then, this species has dispersed to 36 additional southeastern and mid-Atlantic states of the United States. *Aedes albopictus* is a daytime biting mosquito also known as the Asian tiger mosquito and is a nuisance as well as a potential disease vector. This species is reported to vector at least 22 arboviruses, including dengue, chikungunya, and yellow fever. The establishment of this species in the southeastern and mid-Atlantic states of the United States, combined with increasing number of travelers to arbovirus endemic countries that return infected, is a concern for both mosquito control and public health officials. This situation increases the risk of local transmission of arbovirus diseases as observed through autochthonous transmission of dengue and/or chikungunya in Hawaii, USA, France, Croatia, and Italy.

*Aedes albopictus* is currently the most invasive mosquito in the world due to its ability to thrive in both tropical and temperate climates. In its native habitat in Asia *Aedes albopictus* prefers rural environments, where it is found at the edge of forests. In the exotic range, however, its strong ecological flexibility has resulted in rapid adaptation to urban environments where it explores a broad range of water-holding containers, especially small pockets of water in buckets and other artificial containers ubiquitous in private yards. *Aedes albopictus* can reach high densities and is a pestiferous biter, generating many service requests to local mosquito control programs. Clearly, a need exists for better control and eradication of such pests.

SUMMARY OF THE INVENTION

In accordance with the present invention, a heterodissemination method for eradicating a target insect infestation, wherein said insects are harmful to humans or livestock is provided. An exemplary method comprises providing a container comprising a heterospecific, non-harmful insect population having the same habitat as said target insect species of interest; contacting the heterospecific insect population with an insect growth regulator (IGR), said IGR being toxic to said target insect population; and placing the container in the vicinity of one or more target insect larval habitats under conditions whereby the heterospecific insects migrate to, and contaminate the target insect habitat with said IGR; said contamination killing target insect larvae in said habitat, thereby controlling said target insect infestation. In a preferred embodiment, the target insect is a mosquito and the heterospecific insect is a non-biting midge. In another embodiment, the target insect is a house fly and the heterospecific insect is a soldier fly. Several different IGRs are disclosed herein and include, without limitation, synthetic insect juvenile hormone, a chitin synthesis inhibitor, anti juvenile hormone, bacterial and fungal species which are harmful to said target insects and molting disruptors.

Figure 3:

The heterospecific insects can be treated with an IGR containing oil formulation, or both an IGR containing oil formulation and an IGR containing powder formulation as described herein below.

In another embodiment, rather than a heterospecific insect, species which also occupy the mosquito habitat are employed to deploy the IGR. For example, an IGR containing pellet, capsule or gel can be affixed to frogs or toads or other aquatic vertebrates, which then released into the mosquito habitat and disseminate the IGR into mosquito habitat.

In yet another aspect, a larvicidal formulation for coating heterospecific insects comprising an oil formulation containing between 10 and 40% pyriproxyfen, between 50 and 85% methylated seed oil as carrier and between about 5 and 20% polysorbate 20 as emulsifier is also disclosed. The invention also provides a larvicidal powder formulation for coating heterospecific insects containing between 40 to 80% pyriproxyfen, between 15 and 45% fumed silica as carrier and between 5 and 20% Sodium Dodecyl Sulfate as emulsifier, wherein the particle size is optionally milled to between 0.1 to 10 micron with ball mill machine. As mentioned above, these formulations may be used alone or in combination. They may also include one or more IGRs. Other larvacides useful in the present invention, include, without limitation, diflubenzuron, spinosad and application of *Bacillus thuringiensis.*

In another embodiment of the invention, an apparatus for application of IGR to heterospecific insects is provided. An exemplary apparatus comprises a treatment chamber, the chamber comprising a spray hole for application of IGR to heterospecific insects of interest, said chamber having an air permeable cage contained within said chamber, said cage housing a population of heterospecific insects to be treated with said IGR.

BRIEF DESCRIPTION OF THE DRAWINGS

FIG. 1. A schematic diagram of a treatment chamber. *Chironomus* adults were transferred in the mesh cage before moved to the treatment chamber. The spray hole enables the user to spray pesticide formulation right before the cage with *Chironomus* adults is placed on the bottom of the chamber.

FIG. 2. Mosquito pupal mortality achieved by releasing oil treated 20 *Chironomus* adults in a 30 $m^3$ room for 2 days against 10 sentinel cups. The average pupal mortality of *Aedes albopictus* was 88±3.5%.

FIG. 3. Room release of 20 treated *Chironomus* against 10 sentinel cups (5 open and 5 cryptic).

Figure 4:
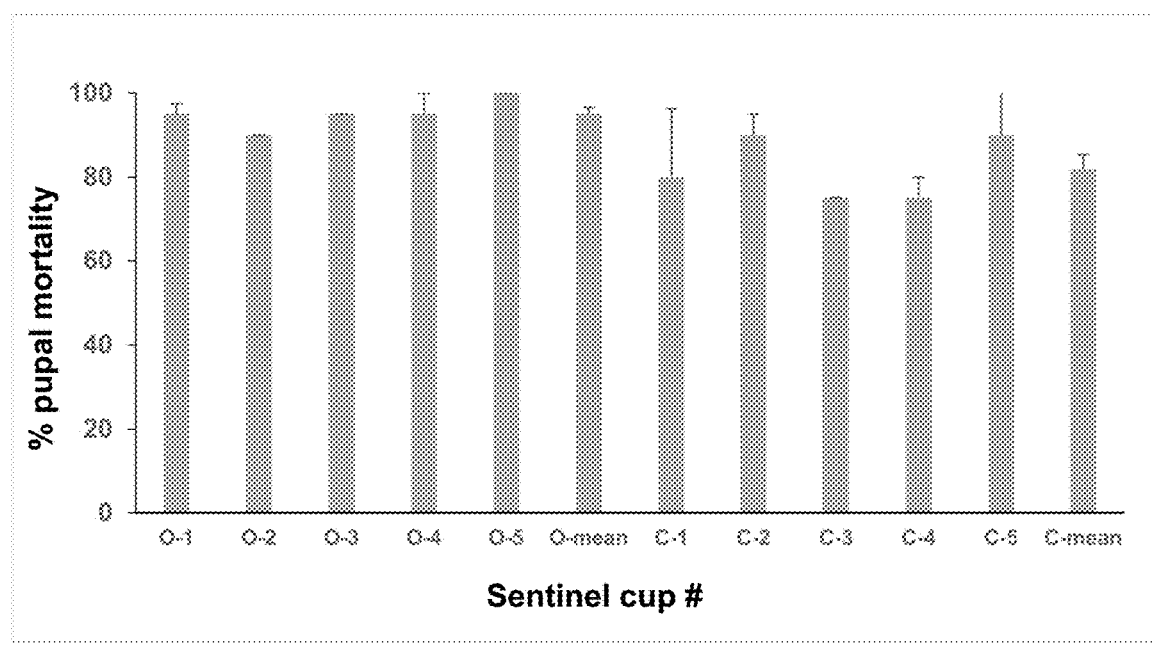

FIG. 4. Mosquito pupal mortality achieved by releasing oil treated 20 *Chironomus* adults in a 30 m$^3$ room for 2 days against 10 sentinel cups (5 open and 5 cryptic). The average pupal mortality of *Aedes albopictus* was 83.75±4.7%. No significant differences were observed between open and cryptic cups.

Figure 5:
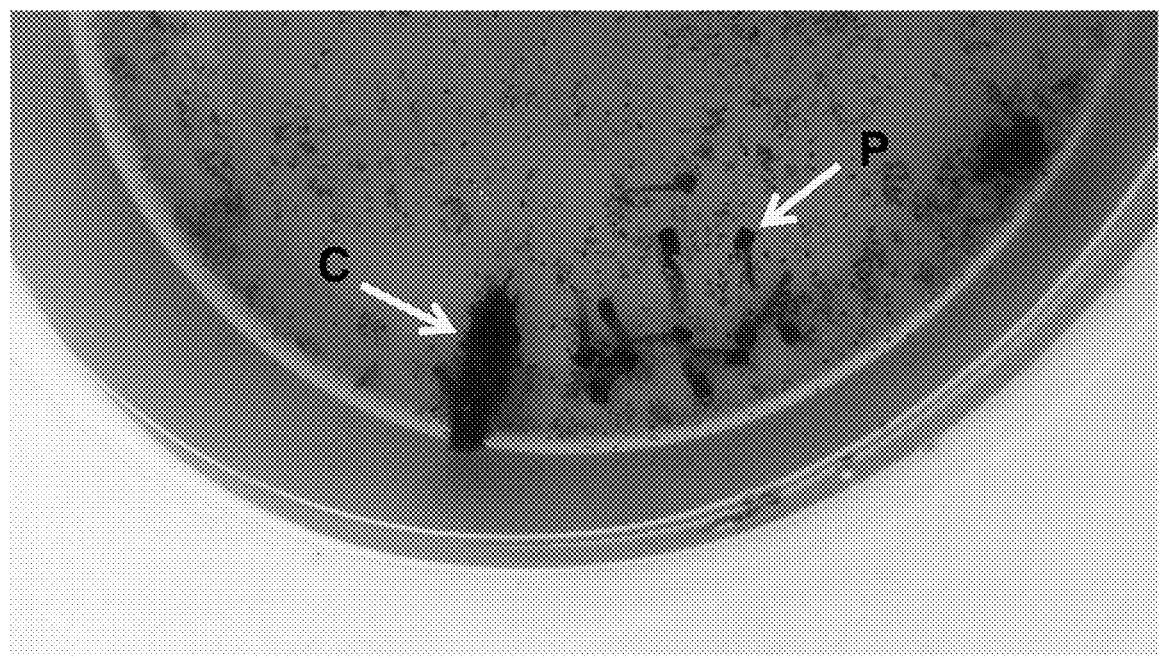

FIG. 5. Larva of *Chironomus* inside a case (C) indicating the *Chironomus* female had visited the cryptic sentinel cup and laid eggs. Dead pupae (P) of *Aedes albopictus* showed the transfer of pyriproxyfen. Residue analysis showed that 0.592-2.06 ppb of a.i in containers with 250 ml oak infusion.

FIGS. 6A and 6B. Female *Chironomus* treated with oil first followed by powder with UV florescent dye. FIG. 6A: under regular light. The upper left picture showed enlarged antenna and particles attached (red arrow). FIG. 6B: under UV light. The upper right picture showed enlarged antenna and particles attached (red arrow: bright spots). Bright spots indicated attached particles all over the insect. Each adult can carry as much as 0.036 mg of a.i. after treatment.

FIG. 7. Semi-field release tunnel showing the tunnel setup site and internal dimension (A; 50×3×2 m) and each of the 10 sentinel sups setup inside a tube (B) to create cryptic habitat.

Figure 8:
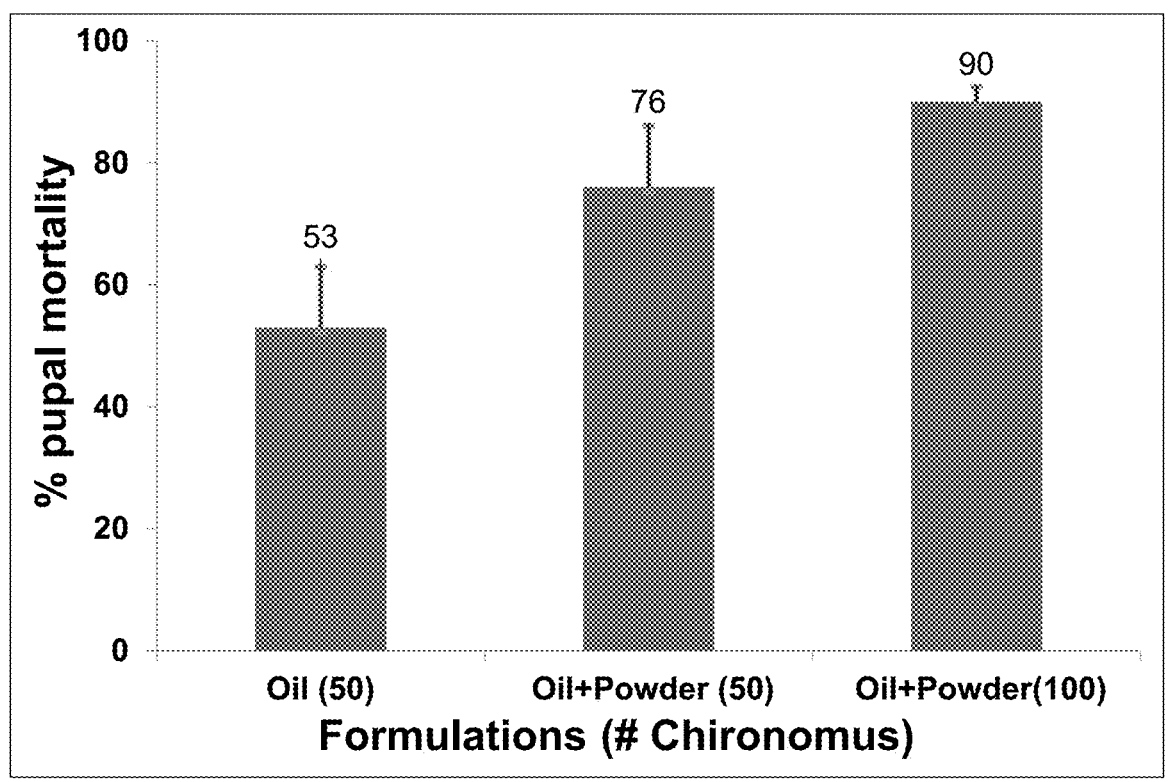

FIG. 8. Pupal mortality of *Aedes albopictus* caused by releasing 50 or 100 treated *Chironomus* females in a meshed tunnel (50×3×2 m) for 5 days.

Figure 9A:
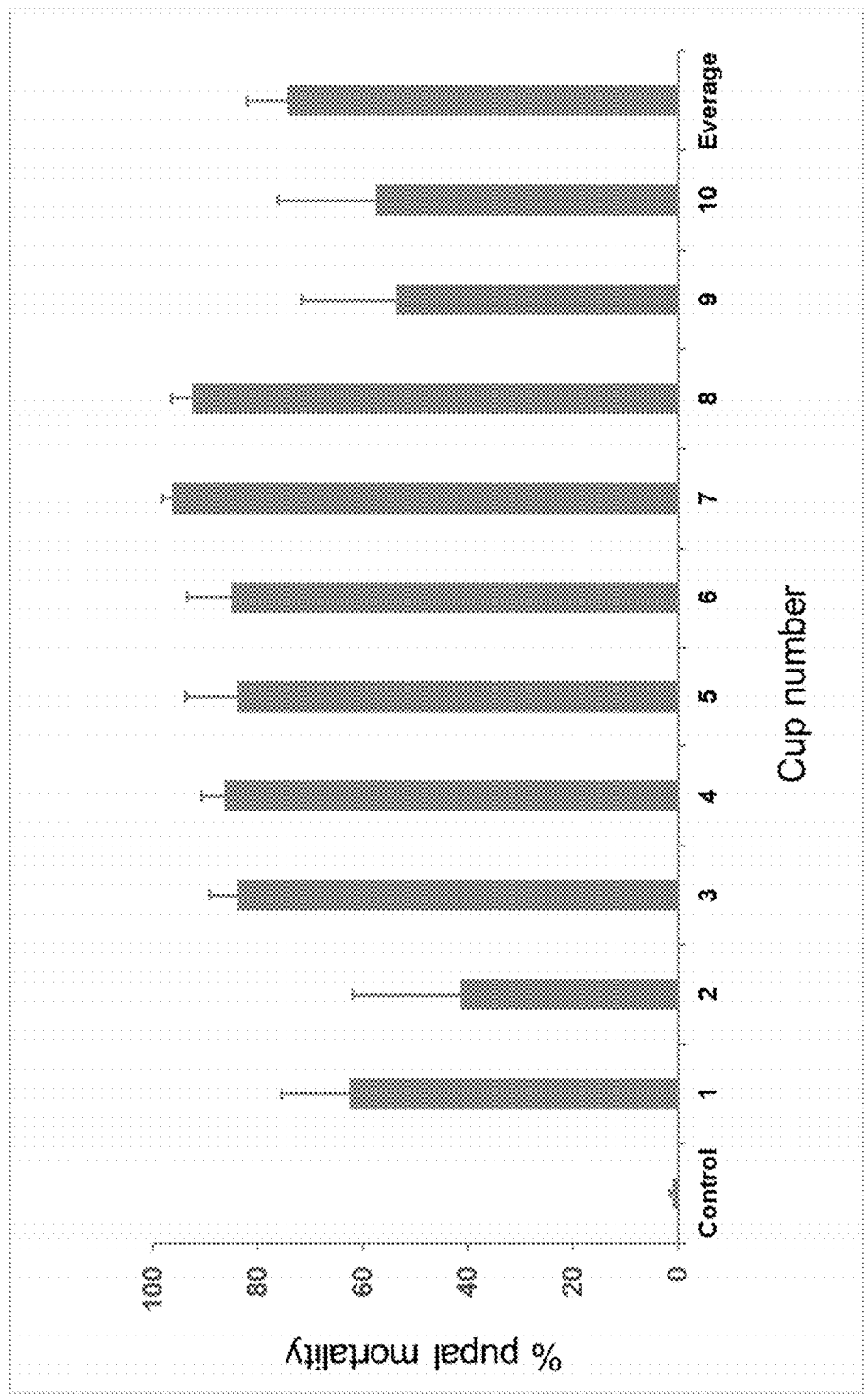
Figure 9B:
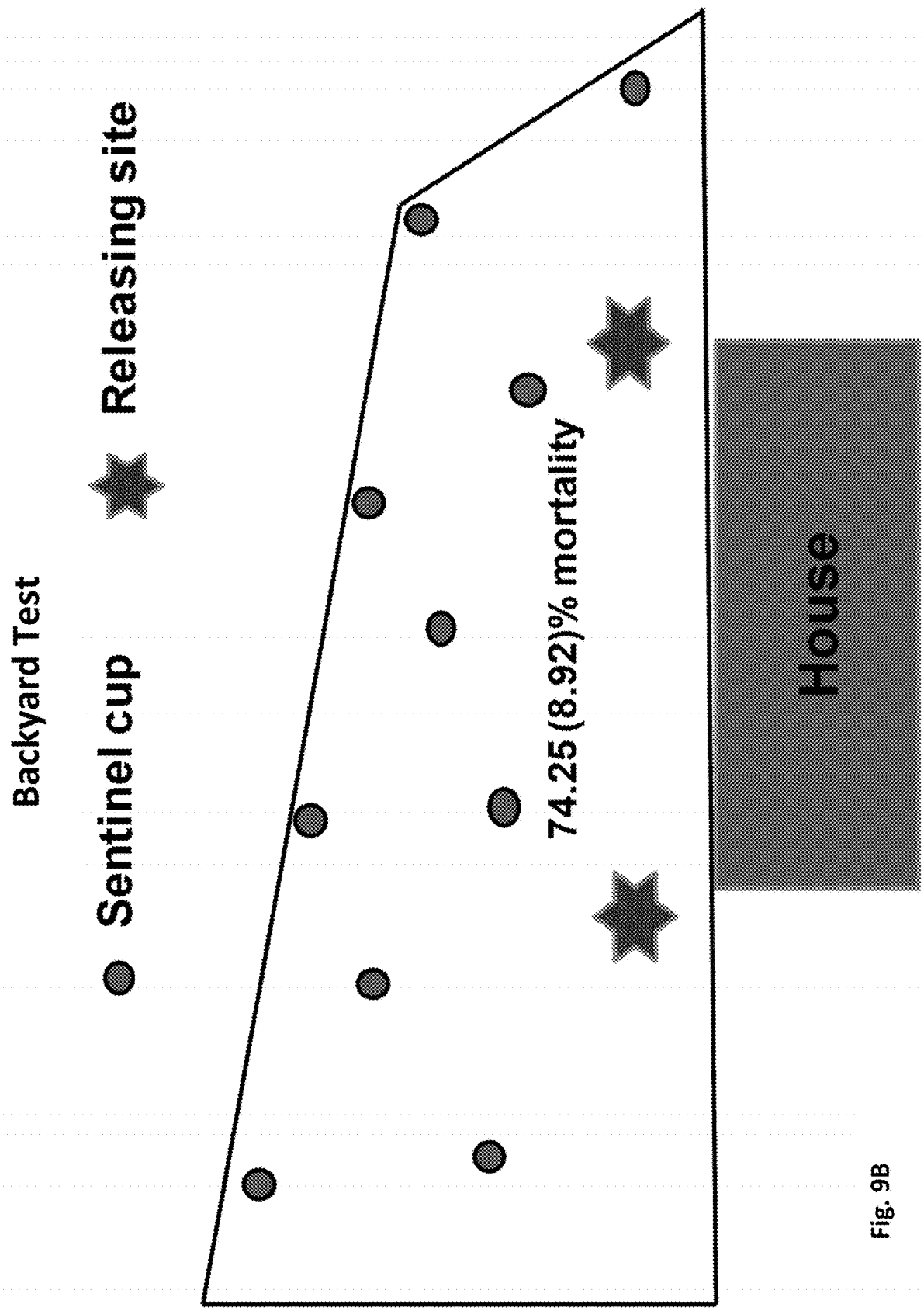

FIGS. 9A and 9B. FIG. 9A: A graph showing pupal mortality of *Aedes albopictus* in each of the 10 sentinel cups tested in a fenced backyard by treat and release of 800 chironomid adults. FIG. 9B: A schematic of the backyard treatment protocol.

FIG. 10. A schematic overview of the method for controlling targeted mosquito populations with midges coated with one or more pesticide formulations.

DETAILED DESCRIPTION OF THE INVENTION

Insect pest control is important to human health, economies (tourism, livestock, real estate), and specific areas such as military, recreation and medical globally. Disease organisms transmitted by mosquitoes for example, include, without limitation, West Nile virus, St. Louis encephalitis virus, Eastern equine encephalomyelitis virus, Everglades virus, Highlands J virus, La Crosse Encephalitis virus in the US; dengue fever, yellow fever, Zika virus, Ilheus virus, malaria, Rift Valley fever, Japanese Encephalitis, chikungunya, malaria; and Murray Valley encephalitis in Australia. House flies are also considered as a pest and are responsible for food contamination and a number of other illnesses.

Due to the short residual-life of the chemicals and mosquito varying habitats, conventional methods of mosquito control are deficient, and pest populations rebound soon after the intervention. Auto-dissemination and treated male mosquito release technology are population dependent, requiring high population densities to be effective. Controlling fly populations likewise is notoriously difficult.

A new and efficient system for treating and controlling mosquito larval habitats using heterospecific insects as a carrier of appropriate pesticide is described. In the case of mosquitos, the relevant insect species is *Chironomus decorus*, non-biting midges with a global distribution and larvae which co-habit with many mosquito species. FIG. 10 provides a schematic overview of the mosquito control system encompassed by the present invention. As shown in the FIG. 10, a container such as that shown in FIG. 1 is utilized to treat midges with the pesticidal coating of the invention which is safe for adult midges. Once the midges are so treated, they are placed in the vicinity of the mosquito population to be reduced or eradicated. The midges, attracted to the cryptic habitat of the mosquitos, migrate to the water where they deliver the pesticide, thereby killing the mosquito larvae or inhibiting adult emergence. Notably, the IGR is also toxic to midge larvae and prevents their emergence.

The above described system can also be adapted to control unwanted house fly infestations.

The following definitions are provided to facilitate an understanding of the invention. They are not intended to limit the invention in any way.

A "heterospecific insect" refers to an insect population different than the target species. The heterodissemination technique described herein utilizes heterospecific insects that are not harmful to humans and can be employed to contaminate habitats of harmful insects such as mosquitos, house flies and other insect pests due to the sharing of similar habitats. This is in contrast to an autodissemination method where the same species to be targeted is also the carrier of the IGR.

"Mosquito" is understood to refer to any specie of the ~3,500 species of the insect that is commonly associated with and given the common name "mosquito." Mosquitoes span 41 insect genera, including the non-limiting examples of *Aedes, Culex, Anopheles* (carrier of malaria), *Coquillettidia*, and *Ochlerotatus*. In embodiments described herein, a mosquito can refer to an adult mosquito, a mosquito egg, a larval mosquito, a pupa or all stages. Thus, some embodiments encompass methods or compositions wherein the insecticidal activity is as a mosquito "adulticide" or alternatively a mosquito "larvicide." Suitably, the compositions and methods described herein function as larvicides.

*Chironomus*, exemplified herein are representative the family Chironomidae which consists of over 10000 species in this family with majority sharing the larval habitat of mosquitos.

The term "binder" as used herein refers to a material used to impart cohesive qualities that offers stability and maintains shape and integrity to a substance ensuring that the substance remains intact during or after manipulation.

The term "carrier" as used herein describes a material that does not cause significant irritation to an organism and does not abrogate the biological activity and properties of the active compound of the composition of the described invention. Carriers must be of sufficiently high purity and of sufficiently low toxicity to render them suitable for administration. The carrier can be inert, or it can have beneficial effects. The terms "excipient", "carrier", or "vehicle" are used interchangeably to refer to carrier materials suitable for formulation and administration of compositions described herein. Carriers and vehicles useful herein include any such materials know in the art which are nontoxic and do not interact with other components.

The term "contained" as used herein refers to the characteristic of being held within a confined area and not prone to being dispersed.

The term "diluent" as used herein refers to an agent that is used to increase the bulk of the active ingredient without affecting the biological effect of the active ingredient.

The term "emulsifiers" as used herein are agents that promote the formation and stabilization of an emulsion.

The term "emulsion" as used herein refers to a two-phase system prepared by combining two immiscible liquid carriers, one of which is dispersed uniformly throughout the other and consists of globules that have diameters equal to or greater than those of the largest colloidal particles. The globule size is critical and must be such that the system achieves maximum stability. Usually, separation of the two phases will occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil.

The term "foraging" as used herein refers to insect behavior for seeking food.

The term "glue-like" as used herein describes the sticky nature of the formulation that makes it difficult for the insect to remove or dislodge it.

The term "insect" as used herein means an arthropod in the class Insecta, characterized by six legs, up to four wings, and a chitinous exoskeleton.

The term "insect-growth regulator" ("IGR") as used herein means a synthetic chemical similar to insect juvenile hormone, which, in some insect species, possesses the same function as native insect juvenile hormone in inhibiting insect life cycle. For example, IGRs regulate insect growth by structurally mimicking insect juvenile hormone. Exemplary insect species that can be controlled by the use of IGRs include, but are not limited to, mosquitoes, grasshoppers, true bugs, flies, fleas, bees, wasps, ants, lice, moths, and beetles. Additional species include any member of Arthropoda. Exemplary IGRs include but are not limited to pyriproxyfen. Other IGRs suitable for use in the invention include, without limitation, chitin synthesis inhibitor, molting disruptor, anti juvenile hormone analog, and juvenile hormone analogs.

The term "overwintering" as used herein refers to the insect behavior of seeking shelter in sites (overwintering sites), such as under loose bark of trees, fallen leaves and other ground debris, to pass through cold winter conditions.

The term "particle" or "particulate" as used herein refers to an extremely small constituent, a minute portion, piece, fragment, or amount that may contain in whole or in part at least one active ingredient as described herein.

The term "peridomestic" as used herein refers to being of or pertaining to living in and around human habitations.

The term "site of application" as used herein refers to a position or location within the target aqueous body where the gel formulation of the composition is released from the insect body part.

The term "solution" generally is considered as a homogeneous mixture of two or more substances. It is frequently, though not necessarily, a liquid. In a solution, the molecules of the solute (or dissolved substance) are uniformly distributed among those of the solvent.

The term "solvent" as used herein refers to a substance capable of dissolving another substance (termed a "solute") to form a uniformly dispersed mixture (solution).

The term "stabilizer" as used herein refers to a substance that is used to preserve the physical, chemical, and other specifications of an active ingredient against physical, chemical or any other biochemical process which would reduce the biological effect of the active ingredient, e.g., preventing larvae from developing into adulthood.

The term "surfactant", as used herein, refers to a surface-active agent that acts to reduce surface tension, which is the elastic like force existing in the surface of a body, e.g., a liquid, at an interface between two liquids, or that between a liquid and a solid, tending to minimize the area of the surface, caused by asymmetries in the intermolecular forces between surface molecules. Surfactants usually are organic compounds that contain both hydrophobic groups and hydrophilic groups, i.e., are amphiphilic. Surfactants can be anionic, cationic, nonionic, and zwitterionic.

As used herein, "Technical pyriproxyfen" is a commercially available concentrated form of pyriproxyfen.

As used herein, the terms "topical" and "topically" are used interchangeably to refer to delivery of an insect growth regulator onto one or more surfaces of an insect's body part, including epithelial surfaces.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including but not limited to") unless otherwise noted. All methods described herein can be performed in any suitable order unless otherwise indicated herein or otherwise clearly contradicted by context.

The following examples are provided to illustrate certain embodiments of the invention. They are not intended to limit the invention in any way.

EXAMPLES

Container mosquitoes such as *Aedes albopictus* and *Aedes aegypti* are vectors of dengue and chikungunya viruses and can support more than 30 arboviruses. Vector control for these mosquitoes is mainly adulticide and larvicide interventions. However, due to the short residual-life of the chemicals and mosquito preference to cryptic habitats, conventional methods of mosquito control are often unsuccessful and populations rebound soon after the intervention. Autodissemination and treated male mosquito release technology are mosquito population dependent, which need high population density to be effective. They can be unsuitable for proactive mosquito control in chronical area.

Figure 2:
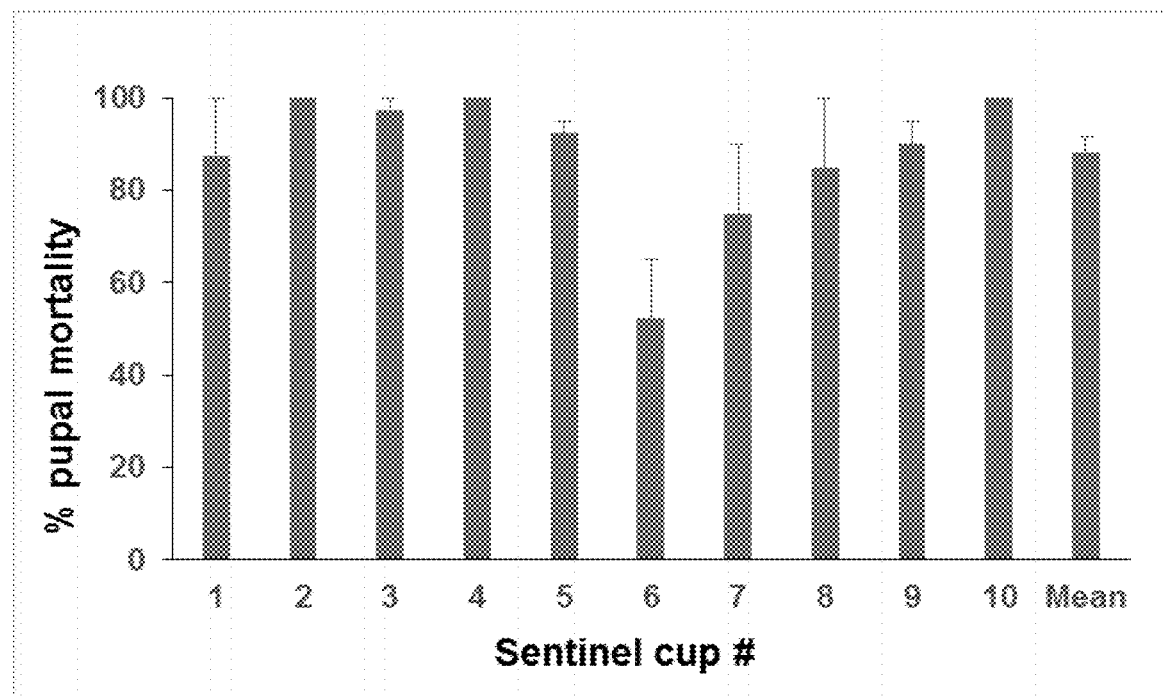

We have demonstrated, in room, semi-field and backyard assays, an easy and efficient technology of treating mosquito larval habitat using heterospecific insects, a different species (*Chironomus decorus*) which shares the same habitat of mosquito larvae. *Chironomus* females don't need blood feeding and the larvae are easy to culture. In a room (30 m$^3$) assay, we have demonstrated an 88.5±3.5% average pupal mortality of *Aedes albopictus* by releasing only 20 pyriproxyfen treated females of *C. decorus* against 10 ovicups each containing 250 ml oak infusion water within 48 hour exposure (FIG. 2) We also received the similar efficacy against cryptic habitat in the same room assay (FIGS. 3, 4). The larvae developed in cryptic sentinel cups indicated the treated female has visited the cup and laid eggs. In the same cup, pupal mortality of *Aedes albpictus* indicated the pyriproxyfen transfer (FIG. 5). We further challenged the technology in a meshed tunnel (50×3×2 m) setup in the field with 10 cryptic sentinel cups inside (FIG. 7) by releasing 50 treated *C. decorus* females for 5 days. Our result showed that with oil treatment only, average pupal mortality of *Aedes albopictus* was 53% and with oil pluses powder treatment, the pupal mortality increased to 76% (FIG. 8). The backyard experiment was conducted by treating 800 chironomid adults with oil formulation (20% a.i) first and followed with powder formulation (60% a.i) at a separate location to avoid contamination. In this experiment, the active ingredient (a.i.) was pyriproxyfen. In order to avoid any dew effect, release time was in the afternoon between 2 to 5 pm. Ten sentinel cups containing 250 ml oak infusion were left in the field for 3 days after release and then taken to the lab for bioassay. Control group was done in the same backyard before the release. There was almost no pupal mortality (1.0 (0.63)%) in the control group.

Chironomus Treatment and Release

Adults (males and females) of *C. decorus* (0 to 2 days old) will be collected and stored in a cage constructed with metal window screen. The oil formulation containing 20% of pyriproxyfen was sprayed through the spray hole into the treatment chamber (FIG. 1) with an airbrush. In one embodiment, a PointZero AirBrush can be sprayed for 3 seconds before the introduction of the cage into the chamber to avoid large droplets getting into the cage. The floating droplets will be allowed 20 min to set. The cage with contaminated *Chironomus* then will be removed from the bottom of the chamber and ready for release in cases where only oil treatment is desired. When a combination oil/powder treatment approach is desired, the cage will be treated in the next chamber. A similar chamber was dusted with powder formulation as described below through the spray hole using a hand duster, such as a B&G Bulb Hand Duster, for 3 seconds before introduction of the cage containing oil treated *Chironomus* adults. The cage then was allowed 10 min in the Chamber for the dust to set before removal of the cage from the bottom of the chamber. The particles attached on the body of *Chironomus* should be visible under a UV light (FIG. 6). The cage was lightly shaken to remove any powder particles attached to the cage to avoid contamination before the cage was moved to the release point. The cage can be located on ground, raised to a certain height or carried into air by an unmanned aerial vehicle (UAV) for targeted release into mosquito breeding hotspot areas.

Formulation

We have developed specific formulations for these purposes which include the following active ingredients.
a) one or more Insect growth regulators (IGR) (pyriproxyfen, methoprene, diflubenzuron, novaluron, precocene, azadirachtin) and bio-pesticide such as *Bacillus thuringiensis israelensis* (Bti), *Bacillus sphaericus* (Bs), *Beauveria bassiana:* 5-20%
b) Carrier: vegetable oil, methylated seed oil, glycerols: 40-70%; and
c) Emulsifier: Tween 20, Tween 80, SDS: 5-10%

Exemplary powder formulations include as active ingredients:
a) one or more Insect growth regulators (IGR) (pyriproxyfen, methoprene, diflubenzuron, novaluron, precocene, azadirachtin) and bio-pesticide such as *Bacillus thuringiensis israelensis, Bacillus sphaericus, Beauveria bassiana:* 40-60% as above, these can be used alone or in combination.
b) Carrier: silica powder: 20-30%; and
c) Emulsifier: SDS: 5-15%

Particle size can be from 0.1 to 10 microns, between 0.5 to 1 microns, between 1 to 3 microns, between 3 to 7 microns and between 7 to 10 microns. A particularly preferred oil formulation comprises 20% pyriproxyfen as a.i, 72% methylated seed oil as carrier and 8% polysorbate 20 as emulsifier.

A particularly preferred powder formulation comprises 60% pyriproxyfen as a.i, 28% fumed silica as carrier and 12% Sodium Dodecyl Sulfate as emulsifier. The particle size was milled to 1 to 10 micron with ball mill machine.

CONCLUSION

The following features illustrate the improvements to current methods of mosquito control offered by the invention described herein:

(1) Proactive against container mosquitoes: With the culture of the carrier species maintained, mosquito control agencies can treat a hotspot area prior to mosquito recovery from overwintering. Treatment early in the season should be efficient to suppress the initial population. If mosquito density appears to increase at any time, the treatment can be repeated as needed.

(2) Effective against cryptic habitats: *Chironomus* adults successfully transferred the IGR to cryptic habitats since their larvae share the same habitat with container mosquito larvae. While pyriproxyfen is exemplified herein as active ingredient, or a.i., other IGRs are suitable for mosquito eradication in the methods and apparatus of the invention can also be employed. Additionally, insect pathogens such as fungi, bacteria, virus can also be used either separately or mixed with IGR as active ingredient. Cryptic habitats have been shown to be the more favorable breeding site of *Aedes albopictus* and invulnerable to broad cast chemical spray. This technology may added to existing methods for insect pest management (IPM) for economic control against container mosquitoes.

(4) Precision: The targeted technology delivered sufficient amount of pesticide into mosquito breeding sites to kill larvae and, or inhibit adult emergence. It possesses almost no harmful impact to the environment and is not threatening to mammalians or any other beneficial species.

(5) Easy treatment and release: The treatment chamber and its operation are simple. Release can be as simple as open the cage and let the *Chironomus* go by themselves. To cover a larger area, the cage can be elevated by means of a pole or a wire. For targeted release, unmanned aerial vehicle (UAV) could be employed since the insect is a relatively weak flyer.

(6) Suitable for use in inaccessible areas with chronic mosquito problems: Problem areas such as backyards with standing water issues, fenced junkyards which are normally inaccessible to mosquito control authorities can be targeted using the present invention. Release treated *Chironomus* near these areas will cover either open containers or cryptic habitats. It is also suitable for treating urban or semi-urban areas with high incidence of arbovirus disease such as dengue and chikungunya.

REFERENCES

1. Habashy M M (2005) Culture of Chironomid larvae (Insecta-Diptera Chironomidae) under different feeding systems. *Egyptian J. Aquat. Res* 31(2):403-418.
2. Hribar L J, et al. (2004) Mosquito larvae (Culicidae) and other Diptera associated with containers, storm drains, and sewage treatment plants in the Florida Keys, Monroe County, Fla. *Florida entomologist* 87(2): 199-203.
3. Utberg G & Sutherland D (1982) The temporal distribution of *Chironomus decorus* (Chironomidae) in northern New Jersey, 1979. *Journal of the New York Entomological Society:* 16-25.
4. Gaugler R, Suman D, & Wang Y (2012) An autodissemination station for the transfer of an insect growth regulator to mosquito oviposition sites. *Med Vet Entomol* 26(1):37-45.
5. Wang Y, Suman D S, Bertrand J, Dong L, & Gaugler R (2014) Dual—treatment autodissemination station with enhanced transfer of an insect growth regulator to mosquito oviposition sites. *Pest management science.*

6. Shepard, Donald S. et al. "Economic Evaluation of an Area-Wide Integrated Pest Management Program to Control the Asian Tiger Mosquito in New Jersey." Ed. Kristin Michel. *PLoS ONE* 9.10 (2014): e111014. *PMC. Web.* 1 Dec. 2015.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for eradicating a target insect infestation, said target insect infestation being harmful to humans or livestock, comprising;
   a) providing a container comprising a heterospecific, non-harmful insect population having the same habitat as said target insect;
   b) coating the non-harmful insect population of step a) with a first larvicidal formulation comprising an oil formulation, followed by application of a second larvicidal formulation comprising a powder formulation, such that the bodies of said non-harmful insect population are coated with both of said oil and powder formulations; and
   c) placing said container in the vicinity of one or more target insect larval habitats or releasing said coated non harmful insect population under conditions whereby said heterospecific non-harmful insects migrate to, and contaminate said one or more target insect larval habitats with said first and second larvicidal formulations; said contamination killing target insect larvae in said one or more target insect habitats, thereby controlling said target insect infestation.

2. The method as claimed in claim 1, wherein said target insect infestation is a mosquito infestation, the one or more target insect larval habitats are mosquito habitats and
   said heterospecific non-harmful insect population comprises non-biting midges, wherein said container is placed in the vicinity of said one or more mosquito larval habitats under conditions whereby said heterospecific non-biting midges migrate to, and contaminate said one or more mosquito larval habitats with said first and second larvicidal formulations; said contamination killing mosquito larvae in said one or more mosquito larval habitats, thereby controlling said mosquito infestation wherein said oil formulation comprises between 10 and 40% pyriproxyfen, between 50 and 85% methylated seed oil as carrier and between about 5 and 20% polysorbate 20 as emulsifier and said powder formulation comprises between 40 to 80% pyriproxyfen, between 15 and 45% fumed silica as carrier and between 5 and 20% Sodium Dodecyl Sulfate as emulsifier.

3. The method of claim 2, wherein the powder formulation has a particle size milled to between 0.1 to 10 micron with ball mill machine.

4. The method of claim 1, wherein said first larvicidal formulation further contains an IGR selected from a synthetic insect juvenile hormone, a chitin synthesis inhibitor, anti-juvenile hormone and molting disruptors.

5. The method of claim 1, wherein said container is a plastic, mesh, fabric, or cardboard container.

6. The method of claim 1, wherein said heterospecific non-harmful insects are treated with said oil formulation in a treatment chamber comprising a spray hole and an air permeable cage contained within said chamber.

7. A method as claimed in claim 1 for controlling a house fly infestation, wherein said heterospecific, non-harmful insect population comprises soldier flies and said container comprising said heterospecific, non-harmful soldier flies is placed in the vicinity of said one or more house fly larval habitats under conditions whereby said soldier flies migrate to, and contaminate said one or more house fly larval habitats with said first and second larvacidal formulations; said contamination killing house fly larvae in said one or more house fly larval habitats, thereby controlling said house fly infestation.

8. The method of claim 7, wherein said soldier flies are further treated with an IGR in a treatment chamber comprising a spray hole and an air permeable cage contained within said chamber.

9. The method of claim 1, said first larvicidal formulation, said second larvicidal formulation, or both formulations further comprises a larvicide selected from diflubenzuron and spinosad.

10. The method of claim 1, said first larvicidal formulation, said second larvicidal formulation, or both formulations further comprises a larvicide obtained from *Bacillus thuringiensis.*

11. A larvicidal formulation for coating heterospecific insects comprising an oil formulation for use in the method of claim 1 containing 20% pyriproxyfen, 72% methylated seed oil as carrier and 8% polysorbate 20 as emulsifier.

12. A larvicidal powder formulation for coating heterospecific insects for use in the larvicidal powder application of claim 1 containing 60% pyriproxyfen, 28% fumed silica as carrier and 12% Sodium Dodecyl Sulfate as emulsifier, wherein said larval powder formulation has a particle size milled to between 0.1 to 10 micron with a ball mill machine.

13. A population of heterospecific insects coated with an oil formulation containing 20% pyriproxyfen, 72% methylated seed oil as carrier and 8% polysorbate 20 as emulsifier and a powder formulation containing 60% pyriproxyfen, 28% fumed silica as carrier and 12% Sodium Dodecyl Sulfate as emulsifier.

14. An apparatus for application of IGR to heterospecific insects consisting of a treatment chamber with a spray hole for application of IGR to heterospecific insects of interest, an air permeable cage, and a population of heterospecific insects, said chamber having the air permeable cage contained within said chamber, said cage housing the population of heterospecific insects to be treated with said IGR.

15. A method for eradicating a target insect infestation, said target insect infestation being harmful to humans or livestock, comprising;
   a) providing a container comprising a heterospecific, non-harmful insect population having the same habitat as said target insect;
   b) coating the non-harmful insect population of step a) with a first larvicidal formulation comprising an oil formulation, followed by application of a second larvicidal formulation comprising a powder formulation, such that the bodies of said non-harmful insect population are coated with both of said oil and powder formulations; and
   c) placing said container in the vicinity of one or more target insect larval habitats or releasing said coated non harmful insect population under conditions whereby said heterospecific non-harmful insects migrate to, and contaminate said one or more target insect larval habitats with said first and second larvacidal formulations;

said contamination killing target insect larvae in said one or more target insect habitats, thereby controlling said target insect infestation, wherein after coating with said oil and powder formulations, said heterospecific insects carry up to 0.036 mg of active ingredient.

* * * * *